(12) United States Patent
Ye et al.

(10) Patent No.: US 12,047,683 B2
(45) Date of Patent: Jul. 23, 2024

(54) IMAGE ACQUISITION METHOD AND APPARATUS, DEVICE, AND STORAGE MEDIUM

(71) Applicant: TENCENT TECHNOLOGY (SHENZHEN) COMPANY LIMITED, Shenzhen (CN)

(72) Inventors: Jingwen Ye, Shenzhen (CN); Baochang Han, Shenzhen (CN); Xiao Han, Shenzhen (CN)

(73) Assignee: TENCENT TECHNOLOGY (SHENZHEN) COMPANY LIMITED, Shenzhen (CN)

( * ) Notice: Subject to any disclaimer, the term of this patent is extended or adjusted under 35 U.S.C. 154(b) by 211 days.

(21) Appl. No.: 17/510,290

(22) Filed: Oct. 25, 2021

(65) Prior Publication Data
US 2022/0046161 A1   Feb. 10, 2022

Related U.S. Application Data

(63) Continuation of application No. PCT/CN2020/114393, filed on Sep. 10, 2020.

(30) Foreign Application Priority Data

Nov. 12, 2019 (CN) .......................... 201911102745.8

(51) Int. Cl.
*H04N 23/73* (2023.01)
*G02B 21/36* (2006.01)
(Continued)

(52) U.S. Cl.
CPC .......... *H04N 23/73* (2023.01); *G02B 21/365* (2013.01); *G06T 1/0007* (2013.01);
(Continued)

(58) Field of Classification Search
None
See application file for complete search history.

(56) References Cited

U.S. PATENT DOCUMENTS

| 10,713,767 B2 | 7/2020 | Liu |
| 2006/0098237 A1* | 5/2006 | Steinberg ............... H04N 23/68 348/E5.045 |

(Continued)

FOREIGN PATENT DOCUMENTS

| CN | 101064783 A | 10/2007 |
| CN | 101719987 A | 6/2010 |

(Continued)

OTHER PUBLICATIONS

The European Patent Office (EPO) The Extended European Search Report for 20886489.2 Jul. 20, 2022 7 pages.
(Continued)

*Primary Examiner* — Twyler L Haskins
*Assistant Examiner* — Esley J Chiu
(74) *Attorney, Agent, or Firm* — ANOVA LAW GROUP, PLLC

(57) ABSTRACT

This application relates to an image acquisition method and apparatus, a device, and a storage medium, and relates to the field of image processing technologies. The method includes obtaining a first image, the first image being an image acquired by controlling an exposure time of an image acquisition component according to a brightness reference value; obtaining an exposure state of the first image; updating the brightness reference value according to the exposure state of the first image, to obtain an updated brightness reference value; controlling the exposure time of the image acquisition component according to the updated brightness reference value; and acquiring a second image.

18 Claims, 5 Drawing Sheets

(51) Int. Cl.
  *G06T 1/00*  (2006.01)
  *G06T 7/00*  (2017.01)
  *G16H 30/40* (2018.01)
  *H04N 1/40*  (2006.01)
  *H04N 23/71* (2023.01)

(52) U.S. Cl.
  CPC .......... *G06T 7/0012* (2013.01); *G16H 30/40* (2018.01); *H04N 1/40012* (2013.01); *H04N 23/71* (2023.01); *G06T 2207/30004* (2013.01)

(56) References Cited

U.S. PATENT DOCUMENTS

| | | | |
|---|---|---|---|
| 2007/0263097 A1 | 11/2007 | Zhao et al. | |
| 2008/0266424 A1* | 10/2008 | Asoma | H04N 23/73 348/E5.037 |
| 2009/0073287 A1* | 3/2009 | Shimizu | H04N 23/73 348/E9.053 |
| 2010/0079617 A1* | 4/2010 | Kosaka | H04N 23/76 348/229.1 |
| 2012/0000982 A1* | 1/2012 | Gao | G06K 7/146 235/455 |
| 2014/0176754 A1* | 6/2014 | Kodama | H04N 23/743 348/222.1 |
| 2015/0022687 A1* | 1/2015 | Galor | H04N 23/76 348/229.1 |
| 2015/0244916 A1 | 8/2015 | Kang et al. | |
| 2015/0244923 A1 | 8/2015 | Lee et al. | |
| 2016/0156825 A1 | 6/2016 | Dallas et al. | |
| 2018/0124317 A1 | 5/2018 | Liu et al. | |
| 2018/0249070 A1* | 8/2018 | Lau | G06T 1/0021 |
| 2019/0215433 A1 | 7/2019 | Masuda | |
| 2019/0253623 A1 | 8/2019 | Lim et al. | |
| 2022/0103739 A1* | 3/2022 | Lei | H04N 23/73 |

FOREIGN PATENT DOCUMENTS

| | | |
|---|---|---|
| CN | 102523386 B | 1/2014 |
| CN | 103491311 A | 1/2014 |
| CN | 107343156 A | 11/2017 |
| CN | 108055486 A | 5/2018 |
| CN | 109005342 A | 12/2018 |
| CN | 109691091 A | 4/2019 |
| CN | 110661983 A | 1/2020 |

OTHER PUBLICATIONS

The World Intellectual Property Organization (WIPO) International Search Report for PCT/CN2020/114393 Sep. 9, 2020 5 Pages (including translation).

The State Intellectual Property Office of the People's Republic of China (SIPO) Office Action 1 for for 201911102745.8 Sep. 9, 2020 7 Pages (including translation).

The State Intellectual Property Office of the People's Republic of China (SIPO) Office Action 2 for for 201911102745.8 Nov. 19, 2020 8 Pages (including translation).

T. Kuno et al.,"A New Automatic Exposure System for Digital Still Cameras," IEEE Transactions on Consumer Electronics, 1998, 44(1): 192-199. 8 pages.

H. Yang et al., "A new automatic exposure algorithm for video cameras using luminance histogram," Frontiers of Optoelectronics in China, 2008, 1(3-4): 285-291. 7 pages.

C. Zhang et al., "An Automatic Exposure Algorithm Based on Information Entropy," Sixth International Symposium on Instrumentation and Control Technology: Signal Analysis, Measurement Theory, Photo-Electronic Technology, and Artificial Intelligence. International Society for Optics and Photonics, 2006. 5 pages.

The European Patent Office (EPO) The Extended European Search Report for 20886489.2 May 13, 2024 5 Pages.

* cited by examiner

IMAGE ACQUISITION METHOD AND APPARATUS, DEVICE, AND STORAGE MEDIUM

RELATED APPLICATIONS

This application is a continuation application of PCT Application No. PCT/CN2020/114393, filed on Sep. 10, 2020, which in turn claims priority to Chinese Patent Application No. 201911102745.8, entitled "IMAGE ACQUISITION METHOD AND APPARATUS, DEVICE, AND STORAGE MEDIUM" and filed on Nov. 12, 2019. The two applications are both incorporated herein by reference in their entireties.

FIELD OF THE TECHNOLOGY

This application relates to the field of image processing technologies, and in particular, to an image acquisition method and apparatus, a device, and a storage medium.

BACKGROUND OF THE DISCLOSURE

Currently, automatic exposure control is a basic function of many digital cameras, and the function can automatically control an exposure duration to achieve a better exposure effect in an image acquisition process.

In the related art, the automatic exposure control may usually be implemented based on a brightness reference value. For example, in an image acquisition process, a camera controls an exposure time, to achieve an average brightness or a weighted brightness of acquired images to be close to a fixed brightness reference value, so that all images acquired in different environments can achieve a good exposure effect.

However, the foregoing automatic exposure control method in the related art often uses a fixed brightness reference value, resulting in a relatively poor exposure control effect in a complex environment such as the environment under a microscope.

SUMMARY

Embodiments of this application provide an image acquisition method and apparatus, a device, and a storage medium, which can improve an exposure control effect in a complex environment. The technical solutions are as follows:

One aspect of the present disclosure provides an image acquisition method. The method is performed by a computer device, and includes obtaining a first image, the first image being an image acquired by controlling an exposure time of an image acquisition component according to a brightness reference value; obtaining an exposure state of the first image; updating the brightness reference value according to the exposure state of the first image, to obtain an updated brightness reference value; controlling the exposure time of the image acquisition component according to the updated brightness reference value; and acquiring a second image.

Another aspect of the present disclosure provides an image acquisition apparatus, applicable to a computer device. The apparatus includes an image obtaining module, configured to obtain a first image, the first image being an image acquired by controlling an exposure time of an image acquisition component according to a brightness reference value; an exposure state obtaining module, configured to obtain an exposure state of the first image; an adjustment module, configured to update the brightness reference value according to the exposure state of the first image, to obtain an updated brightness reference value; and an acquisition module, configured to control the exposure time of the image acquisition component according to the updated brightness reference value, to acquire a second image.

According to an aspect, a computer device is provided, including a processor and a memory, the memory storing at least one instruction, at least one program, a code set, or an instruction set, and the at least one instruction, the at least one program, the code set, or the instruction set being loaded and executed by the processor to perform: obtaining a first image, the first image being an image acquired by controlling an exposure time of an image acquisition component according to a brightness reference value; obtaining an exposure state of the first image; updating the brightness reference value according to the exposure state of the first image, to obtain an updated brightness reference value; controlling the exposure time of the image acquisition component according to the updated brightness reference value; and acquiring a second image.

Another aspect of the present disclosure provides a non-transitory computer-readable storage medium, storing at least one instruction, at least one program, a code set, or an instruction set, and the at least one instruction, the at least one program, the code set, or the instruction set being loaded and executed by a processor to perform the foregoing image acquisition method.

The technical solutions provided in this application may include the following beneficial effects. A brightness reference value used during acquiring an acquired frame of image is updated according to an exposure state of the previous frame of acquired image, and a next frame of image is acquired according to an updated brightness reference value, so that the brightness reference value is dynamically updated, and an exposure control effect during image acquisition in a complex environment is improved, thereby avoiding a loss of important image detail information of the next frame of image as much as possible.

It is to be understood that the foregoing general descriptions and the following detailed descriptions are merely for illustration and explanation purposes and are not intended to limit this application.

BRIEF DESCRIPTION OF THE DRAWINGS

Accompanying drawings herein are incorporated into this specification and constitute a part of this specification, show embodiments that conform to this application, and are used for describing a principle of this application together with this specification.

DESCRIPTION OF EMBODIMENTS

Figure 1:
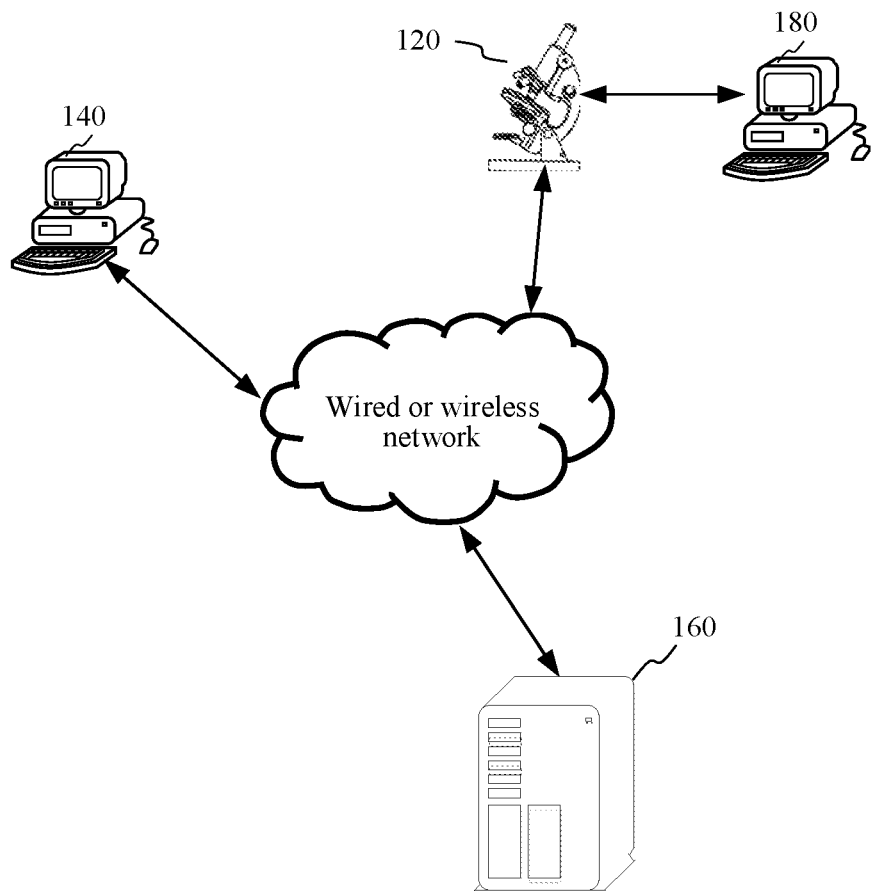
FIG. 1 is a system configuration diagram of an image acquisition system applied to a microscope according to the embodiments of this application.

Exemplary embodiments are described in detail herein, and examples of the exemplary embodiments are shown in the accompanying drawings. When the following description involves the accompanying drawings, unless otherwise indicated, same or similar elements are denoted by same numerals in different accompanying drawings. The implementations described in the following exemplary embodiments do not represent all implementations that are consistent with this application. On the contrary, the implementations are merely examples of devices and methods that are described in detail in the appended claims and that are consistent with some aspects of this application.

It is to be understood that "several" mentioned in this specification means one or more, and "a plurality of" means two or more. "And/or" describes an association relationship for describing associated objects and represents that three relationships may exist. For example, A and/or B may represent the following three cases: only A exists, both A and B exist, and only B exists. The character "/" in this specification generally indicates an "or" relationship between the associated objects.

This application provides an image acquisition method, which can improve an exposure control effect during image acquisition. For ease of understanding, several terms involved in this application are explained below.

(1) Pathological Analysis

Pathological analysis is a pathomorphological method used for examining pathological changes in organs, tissues, or cells of a body, and is a process of examining pathological changes that occur, discussing causes, pathogenesis, and development of the pathological changes, and finally making a pathological diagnosis by adopting a pathomorphological examination method, to explore a pathological process of organs, tissues, or cells.

The pathomorphological examination method may include processes of first observing a pathological change of a gross specimen, then cutting a tissue of the pathological change of a specific size, making a pathological section by using a histopathological method, and then further examining the pathological change by using a microscope.

Pathological analysis is a gold standard for diagnosis, prognostic analysis, and guiding cancer treatment. Currently, there is a talent gap of pathologists, and the gap is increasing year by year, which leads to heavy tasks for pathologists, and the distribution of medical resources cannot be balanced. Therefore, the digitalization of pathological sections based on an optical microscope and an artificial intelligence (AI) assisted diagnosis system gradually become the focus of attention and have a wide range of application prospects. For example, automatic image storage and image-based real-time AI-assisted diagnosis can assist doctors in completing target tasks, thereby effectively improving the work efficiency. In another example, remote sharing of a field of view of a microscope has important application value in fields such as teaching and telemedicine. Using an image acquisition component (such as a camera) to perform image acquisition in the field of view of the microscope for pathological analysis is the first step of such microscope tasks. Automatic exposure control of the camera is an important guarantee for quality of acquired images.

(2) Artificial Intelligence (AI)

AI is a theory, a method, a technology, and an application system that use a digital computer or a machine controlled by the digital computer to simulate, extend, and expand human intelligence, perceive an environment, obtain knowledge, and use knowledge to obtain an optimal result. In other words, the AI is a comprehensive technology of computer science, which attempts to understand the essence of intelligence and produces a new intelligent machine that can react in a manner similar to human intelligence. The AI is to study the design principles and implementation methods of various intelligent machines, so that the machines have the functions of perception, reasoning, and decision-making.

The AI technology is a comprehensive discipline, and relates to a wide range of fields including both hardware-level technologies and software-level technologies. The basic AI technologies generally include technologies such as a sensor, a dedicated AI chip, cloud computing, distributed storage, a big data processing technology, an operating/interaction system, and electromechanical integration. AI software technologies mainly include several major directions such as a computer vision (CV) technology, a speech processing technology, a natural language processing technology, and machine learning/deep learning. The solutions provided in the embodiments of this application mainly relate to technologies such as ML/deep learning of the AI.

(3) Machine Learning (ML)

ML is a multi-field interdiscipline, and relates to a plurality of disciplines such as probability theory, statistics, approximation theory, convex analysis, and algorithm complexity theory. The ML specializes in studying how a computer simulates or implements a human learning behavior to obtain new knowledge or skills, and reorganize an existing knowledge structure, to keep improving performance of the computer. The ML is the core of the AI, is a basic way of making the computer intelligent, and is applied to fields of the AI. The ML and deep learning generally include technologies such as an artificial neural network, a belief network, reinforcement learning, transfer learning, inductive learning, and learning from demonstrations.

In a scenario involved in the embodiments of this application, images acquired in an eyepiece field of view of a microscope may be applied to AI-assisted pathological analysis and diagnosis. The AI-assisted pathological analysis and diagnosis usually mean that the images acquired in the eyepiece field of view of the microscope are inputted into a pre-trained machine learning model, and then pathological analysis and diagnosis are made in an automatic or manual manner according to an output result of the machine learning model.

The technical solutions provided in this application can avoid a loss of detail information of the images in the eyepiece field of view of the microscope caused by over-exposure or underexposure as much as possible, so that high-quality microscopic images can be subsequently saved, or high-accuracy pathological analysis and diagnosis can be ensured.

FIG. 1 shows a system configuration diagram of an image acquisition system applied to a microscope according to the embodiments of this application. As shown in FIG. 1, the system includes a microscope 120 and an image processing device 140. In some embodiments, the system further includes a server 160.

The microscope 120 may be an electron microscope integrated with an image acquisition component. The electron microscope further provides an image output interface to the outside. An operator of the microscope 120 acquires a microscopic image in an eyepiece field of view of the microscope 120 according to an image acquisition function of the electron microscope, and imports the microscopic image into the image processing device 140 or the server 160 through the image output interface.

Alternatively, the microscope 120 may be an original optical microscope, and may be externally connected to an image acquisition component (such as a camera or another device integrated with a camera). The image acquisition component may acquire a microscopic image in an eyepiece of the microscope 120.

For example, the microscope 120 may be integrated with a camera obscura. An operator of the microscope 120 may mount the camera on the camera obscura, to capture the microscopic image in the eyepiece of the microscope 120 by using the camera. In some embodiments, the camera is integrated with an image output interface, and the microscopic image captured by the camera may be transmitted to the image processing device 140 or the server 160 through the image output interface.

The image output interface may be a wired interface, such as a universal serial bus (USB) interface, a high-definition multimedia interface (HDMI), or an Ethernet interface. Alternatively, the image output interface may be a wireless interface, such as a wireless local area network (WLAN) interface or a Bluetooth interface.

Correspondingly, according to different types of the image output interfaces, there may be a plurality of manners of exporting the microscopic image captured by the camera. For example, the microscopic image is imported into the image processing device 140 or the server 160 in a wired or a short-range wireless manner, or the microscopic image may be imported into the image processing device 140 or the server 160 by using a local area network or the Internet.

In some embodiments, the system further includes an image acquisition control device 180.

The image acquisition control device 180 may be directly connected to the microscope 120 or connected to the microscope 120 by using a network. For example, the image acquisition control device 180 may be connected to a built-in or external image acquisition component of the microscope 120.

The server 160 is one or more servers, a virtualization platform, or a cloud computing service center.

The server 160 may be a server for providing a backend service for the microscope 120 or an application installed in the image acquisition control device 180. The backend server may provide version management for the application, perform backend processing for a microscopic image obtained by the application, or the like.

In some embodiments, the system may further include a database. The database may be a Redis database, or may be a database of another type. The database is used for storing various types of data, for example, for storing the microscopic image acquired by the image acquisition component.

In some embodiments, the microscope 120 is connected to the image processing device 140 by using a communication network. In some embodiments, the image acquisition control device 180 is connected to the server 160 by using a communication network. In some embodiments, the communication network is a wired network or a wireless network.

In some embodiments, the system may further include a management device (not shown in FIG. 1). The management device is connected to the server 160 by using a communication network. In some embodiments, the communication network is a wired network or a wireless network.

In some embodiments, the wireless network or the wired network uses a standard communication technology and/or protocol. The network is generally the Internet, but may be any network, including but not limited to a local area network (LAN), a metropolitan area network (MAN), a wide area network (WAN), a mobile, wired, or wireless network, or any combination of a dedicated network or a virtual dedicated network. In some embodiments, technologies and/or formats such as hypertext markup language (HTML) and extensible markup language (XML) are used to represent data exchanged through a network. In addition, all or some links may be encrypted by using conventional encryption technologies such as a secure socket layer (SSL), transport layer security (TLS), a virtual private network (VPN), and Internet Protocol security (IPsec). In some other embodiments, custom and/or dedicated data communication technologies may also be used in place of or in addition to the foregoing data communication technologies.

Figure 2:
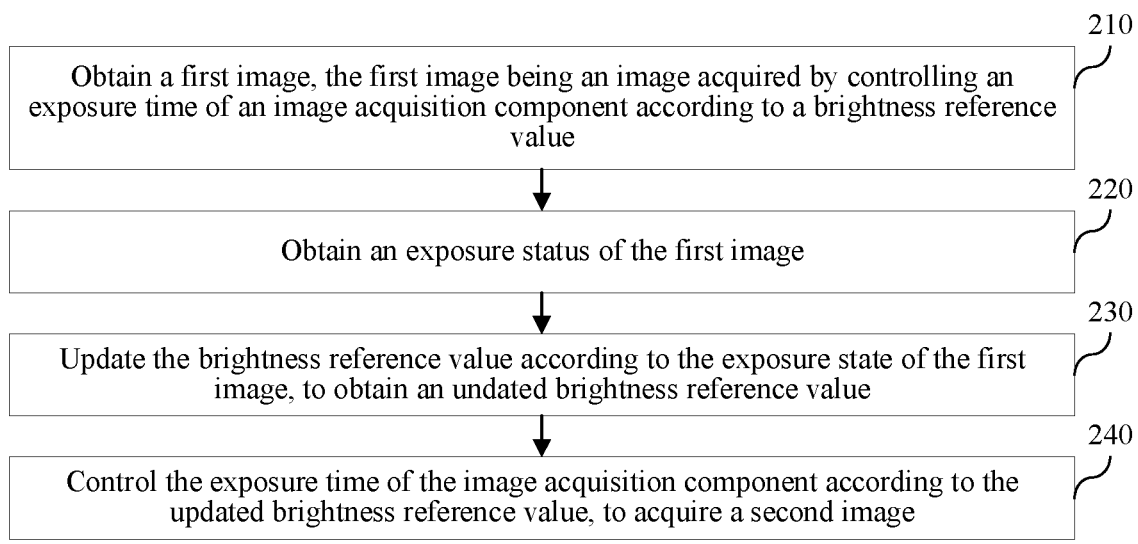
FIG. 2 is a schematic flowchart of an image acquisition method according to an exemplary embodiment of this application.

FIG. 2 shows a schematic flowchart of an image acquisition method according to an exemplary embodiment of this application. The image acquisition method may be performed by a computer device. For example, in a scenario of acquiring an image in an eyepiece field of view of a microscope, the computer device may be the microscope 120 or the image acquisition control device 180 in the foregoing system shown in FIG. 1. As shown in FIG. 2, the image acquisition method may include the following steps:

Step 210. Obtain a latest acquired first image, the first image being an image acquired by controlling an exposure time of an image acquisition component according to a brightness reference value.

In one embodiment, the brightness reference value is a target value of a brightness of an image acquired by the image acquisition component.

In other words, during the acquisition of the first image by the image acquisition component, the computer device controls the exposure time of the image acquisition component, to cause a brightness (for example, an average brightness or a weighted brightness) of the acquired first image to be close to the brightness reference value as much as possible.

Step 220. Obtain an exposure state of the first image.

In one embodiment, after obtaining a previous frame of image (that is, the first image) acquired by the image acquisition component, the computer device may determine an exposure state of the previous frame of image according to brightness distribution of the previous frame of image acquired by the image acquisition component.

In one embodiment, the exposure state of the image is used for indicating an exposure effect of the image.

For example, the exposure state may include, but is not limited to, three exposure states: overexposure, underexposure, and normal exposure.

Step 230. Update the brightness reference value according to the exposure state of the first image, to obtain an updated brightness reference value.

In one embodiment, when the previous frame of image acquired by the image acquisition component is overexposed or underexposed, it indicates that the exposure effect during the previous image acquisition is relatively poor, and the brightness reference value needs to be adjusted. In this case, the computer device may adjust the brightness reference value according to the exposure state.

For example, when the previous frame of image is overexposed, it indicates that the brightness reference value used during the previous image acquisition is excessively high, and the computer device may decrease the brightness reference value according to the overexposed state, to obtain the updated brightness reference value with a lower brightness value.

In another example, when the previous frame of image is underexposed, it indicates that the brightness reference value used during the previous image acquisition is excessively low, and the computer device may increase the brightness reference value according to the underexposed state, to obtain the updated brightness reference value with a higher brightness value.

The computer device may update the brightness reference value according to a fixed step size when increasing or decreasing the brightness reference value. Alternatively, the computer device may calculate a current adjustment range in real time, to update the brightness reference value.

Step 240. Control the exposure time of the image acquisition component according to the updated brightness reference value, to acquire a second image.

In conclusion, according to the solutions shown in one embodiment, the computer device may update a brightness reference value used during acquiring a previous frame of image according to an exposure state of the previous frame of acquired image, and acquire a next frame of image according to an updated brightness reference value, so that the brightness reference value is dynamically updated, and an exposure control effect during image acquisition in a complex environment is improved, thereby avoiding a loss of important image detail information of the next frame of image as much as possible.

Acquiring an image in the field of view of the microscope by using the camera is an indispensable part of various microscope tasks of digital pathological analysis, including: image storage, AI prediction, remote sharing of the field of view of the microscope, and the like. To avoid introducing unnecessary delay into an original workflow of a pathologist during image acquisition by using the camera and subsequent related tasks, the used automatic exposure control method generally needs to meet relatively high real-time performance and stability.

The quality of the image acquired by the camera is closely related to accuracy of subsequent diagnosis, and image detail information may be ignored due to overexposure and underexposure. Therefore, how to select the brightness reference value quickly and appropriately is a core problem to be solved in the automatic exposure control of the camera of the microscope. Actually, brightness changes in the eyepiece field of view of the microscope is much more complex than natural scenes used by an ordinary digital camera. On one hand, there are more factors that affect the brightness of the eyepiece field of view of the microscope. In addition to ambient light and an aperture size, the factors further include a type and brightness of a light source of the microscope, a thickness of an observed object, a magnification of an objective lens, and the like. On the other hand, because operations such as moving the field of view quickly and switching objective lenses with different magnifications are often required in a specific task, short-time changes of the brightness in the field of view of the microscope are more severe. Therefore, directly copying the exposure control method used for the ordinary digital camera may lead to an exposure failure.

For example, if the solution of using the fixed brightness reference value is adopted, for exposure effects in different eyepiece fields of view of the same microscope, when a deeply-stained tissue region occupies a relatively large field of view, overexposure may occur due to an excessively high brightness reference value; and when a light-colored tissue or a blank region occupies a relatively large field of view, underexposure may occur due to an excessively low brightness reference value. Particularly, in the former case, if details of the light-colored tissue are ignored due to overexposure, the subsequent pathological analysis and diagnosis will become greatly troublesome.

According to the foregoing solution shown in FIG. 2, first, the exposure state of the current frame of image is determined according to brightness distribution thereof, and then the brightness reference value of the automatic exposure of the camera of the microscope is adjusted to an adaptive value quickly and adaptively, so that the loss of important image detail information of the next frame of image due to overexposure or underexposure can be avoided as much as possible, to prevent the introduction of unnecessary uncertainty into remote diagnosis and AI-assisted diagnosis made by the pathologist in a subsequent workflow.

In addition to the scenario of acquiring the image in the eyepiece field of view of the microscope, the solutions provided in the embodiments of this application may also be applied to other image acquisition scenarios that require quick and accurate exposure control. For example, the solutions may be applied to scenarios of high frame rate camera types of continuous image acquisition and video surveillance, to achieve adaptive and quick automatic exposure control. Such application scenarios may include: driver status monitoring of a vehicle camera, product quality monitoring of an industrial camera, and the like.

Figure 3:
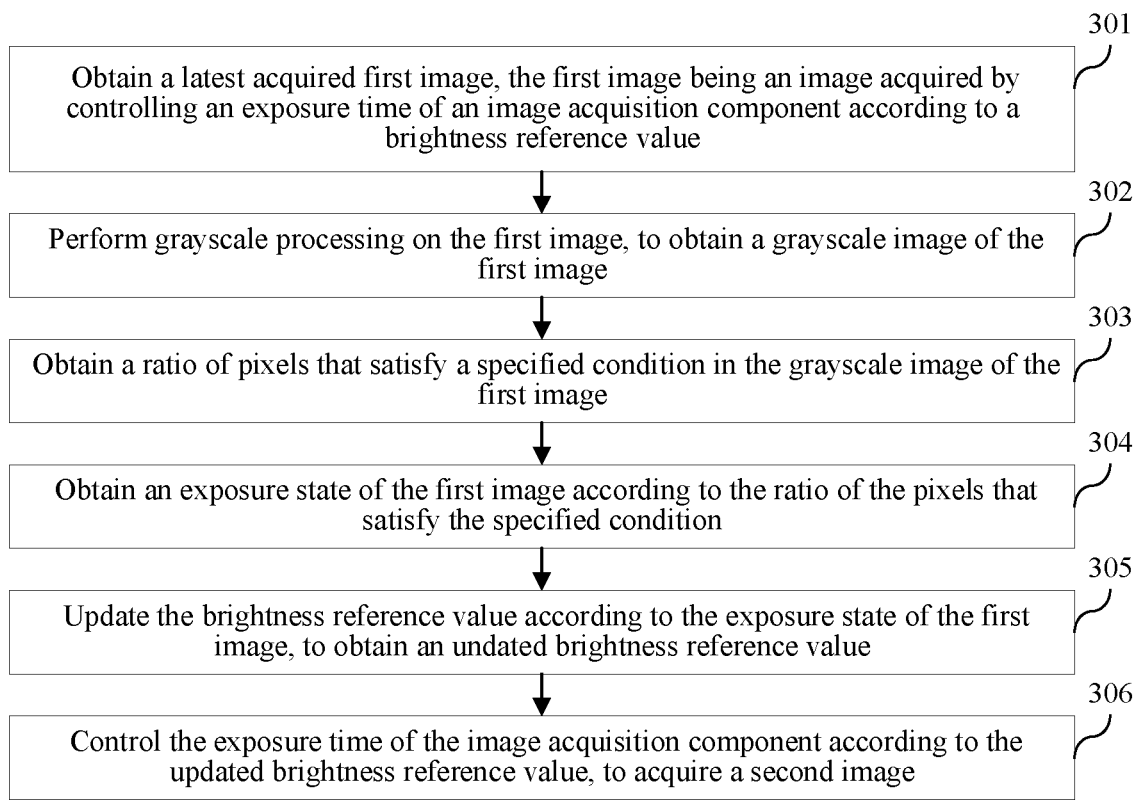
FIG. 3 is a schematic flowchart of an image acquisition method according to an exemplary embodiment of this application.

The scenario in which the solutions provided in the embodiments of this application are applied to image acquisition in an eyepiece field of view of a microscope is used as an example. FIG. 3 shows a schematic flowchart of an image acquisition method according to an exemplary embodiment of this application. The image acquisition method may be performed by a computer device. For example, the computer device may be the microscope 120 or the image acquisition control device 180 in the foregoing system shown in FIG. 1. As shown in FIG. 3, the image acquisition method may include the following steps:

Step 301: Obtain a latest acquired first image, the first image being an image acquired by controlling an exposure time of an image acquisition component according to a brightness reference value, and the image acquisition component being configured to acquire an image in an eyepiece field of view of the microscope.

In one embodiment, the image acquisition component may determine an exposure region in the eyepiece field of view of the microscope automatically or under the control of the computer device, and acquire an image in the determined exposure region.

When acquiring the image in the determined exposure region, the image acquisition component may control the exposure time according to the brightness reference value, to cause a brightness of the acquired image to be close to the brightness reference value.

In the process of determining the exposure region, the image acquisition component may determine a specified region in the eyepiece field of view of the microscope as the exposure region automatically or under the control of the computer device.

Alternatively, in the process of determining the exposure region, the image acquisition component may determine the exposure region automatically or under the control of the computer device according to a preset exposure region determining algorithm.

The exposure region determining algorithm may be an algorithm that recognizes a captured subject position or a region of interest in the eyepiece field of view of the microscope, and determines the exposure region according to the recognized subject position or region of interest. In one embodiment, the exposure region determining algorithm may be an AI algorithm.

The computer device may obtain the first image after the first image is acquired by the image acquisition component. Then, the computer device may determine the exposure state of the first image according to brightness distribution information of the first image. For an exposure state determining process, reference may be made to the subsequent steps.

Step 302. Perform grayscale processing on the first image, to obtain a grayscale image of the first image.

The computer device may perform grayscale image conversion on the first image (that is, convert the first image into the grayscale image) after obtaining the first image, to obtain the grayscale image of the first image.

Step 303. Obtain a ratio of pixels that satisfy a specified condition in the grayscale image of the first image.

In one embodiment, the specified condition may include an overexposure condition and an underexposure condition. The overexposure condition is that a grayscale value is greater than a first grayscale threshold, and the underexposure condition is that a grayscale value is less than a second grayscale threshold.

In one embodiment, the first grayscale threshold may be higher than the second grayscale threshold.

In one embodiment, the computer device may determine a grayscale value of each pixel in the grayscale image after obtaining the grayscale image of the first image, and then determine whether each pixel satisfies the overexposure condition, the underexposure condition, or neither of the two conditions according to the grayscale value of each pixel and the preset first grayscale threshold and second grayscale threshold.

For example, it is assumed that the first grayscale threshold is 200, and the second grayscale threshold is 100. When a grayscale value of a pixel A in the first image is 80, the grayscale value of the pixel A is less than the second grayscale threshold. In this case, it can be determined that the pixel A satisfies the underexposure condition, and the pixel A may also be referred to as an underexposed pixel. When a grayscale value of a pixel B in the first image is 240, the grayscale value of the pixel B is greater than the first grayscale threshold. In this case, it can be determined that the pixel B satisfies the overexposure condition, and the pixel B may also be referred to as an overexposed pixel. When a grayscale value of a pixel C in the first image is 150, the grayscale value of the pixel C is neither less than the second grayscale threshold nor greater than the first grayscale threshold. In this case, it can be determined that the pixel C does not satisfy the overexposure condition and the underexposure condition, and the pixel C may also be referred to as a normal pixel.

Step 304. Obtain the exposure state of the first image according to the ratio of the pixels that satisfy the specified condition.

In some embodiments, the computer device may obtain the exposure state of the first image according to the ratio of the pixels that satisfy the specified condition in the following manner:

1) Obtain that the exposure state of the first image is overexposure in response to that an overexposure ratio is higher than a first ratio threshold, the overexposure ratio being a ratio of pixels that satisfy the overexposure condition in the grayscale image of the first image.

2) Obtain that the exposure state of the first image is underexposure in response to that an underexposure ratio is higher than a second ratio threshold, the underexposure ratio being a ratio of pixels that satisfy the underexposure condition in the grayscale image of the first image.

3) Obtain that the exposure state of the first image is normal exposure in response to that the overexposure ratio is not higher than the first ratio threshold, and the underexposure ratio is not higher than the second ratio threshold.

In one embodiment, the exposure state may be defined first. In some embodiments, the definition and description of the exposure state of the images may be as follows:

| Image status | Status description |
| --- | --- |
| Normal status | The automatic exposure reference value of the current frame is selected reasonably, and the acquired image is exposed normally. |
| Over-exposed state | The automatic exposure reference value of the current frame is selected excessively high, and the acquired image is overexposed. |
| Under-exposed state | The automatic exposure reference value of the current frame is selected excessively low, and the acquired image is underexposed. |

The computer device may evaluate the exposure state of the first image according to the ratio of the overexposed or underexposed pixels in the image.

During using the camera of the microscope for pathological analysis, the value of the optimal brightness reference value of the automatic exposure is different due to different sizes of the deeply-stained tissue region in the current field of view. The conventional method of using the average brightness value or other photometric evaluation functions cannot effectively distinguish whether the brightness of the acquired image mainly results from the shades of the captured subject in the field of view, or mainly results from the strength of the exposure. However, to directly estimate the brightness reference value according to the ratio of the deeply-stained tissue region, it is difficult to extract valid general indicators to distinguish dark pixels due to different types and sources of pathological sections. In addition, considering that for application scenarios of the microscope, it is necessary to avoid the loss of details of the light-colored tissue due to overexposure of the acquired image. Therefore, a more intuitive manner is adopted in one embodiment to determine whether the current frame of image is in an overexposed state according to whether there is a specific quantity of overexposed pixels. Before determining, a color image needs to be converted into a grayscale image, and the grayscale value of each pixel is denoted by g. Then, a pixel with a grayscale value greater than a threshold $Th_1$ is defined as an overexposed pixel, and a ratio $r_1$ of the overexposed pixel in total-image pixels is calculated. A calculation formula is as follows:

$$r_1 = \frac{N[g > Th_1]}{N_{total}}$$

N[α] denotes a quantity of pixels that satisfy a condition α, and $N_{total}$ denotes a quantity of total-image pixels.

Figure 4:
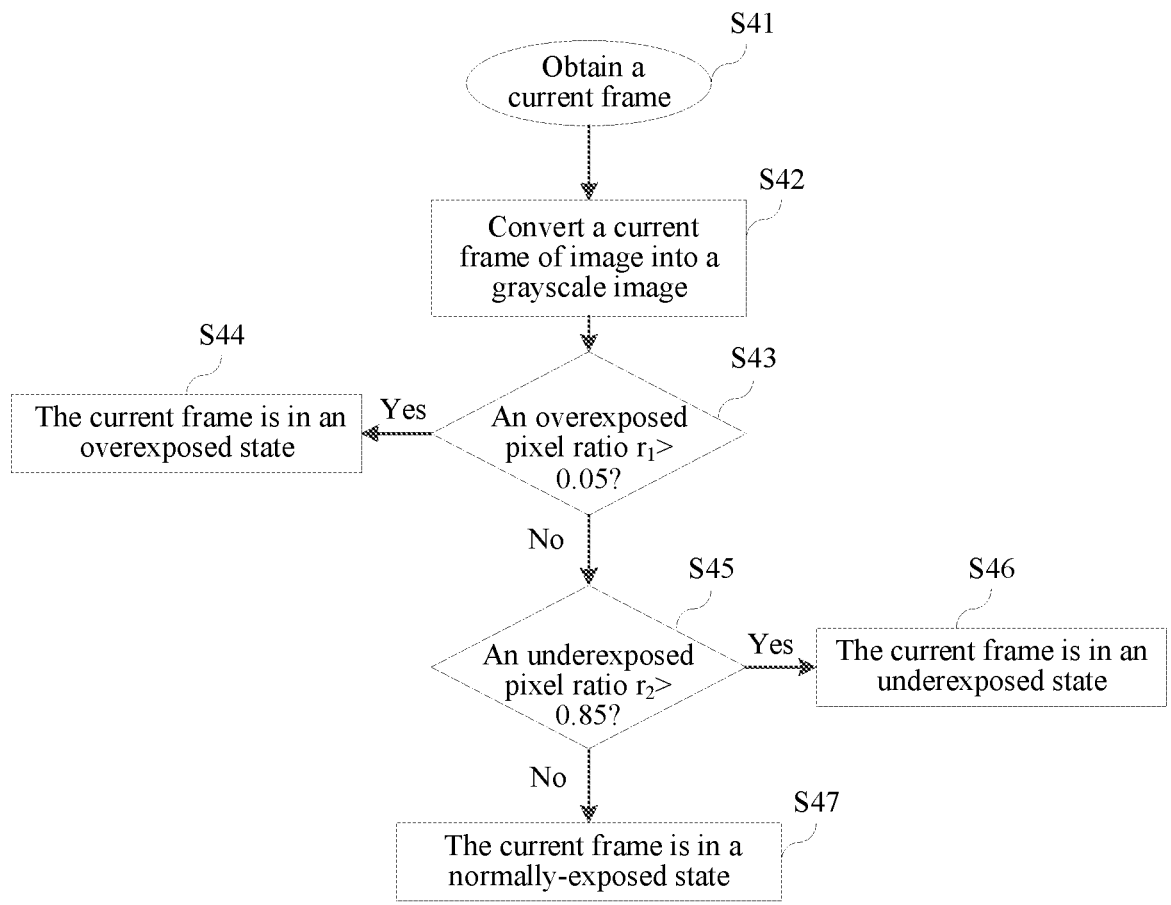
FIG. 4 is a schematic diagram of an exposure state determining process according to the embodiment in FIG. 3.

FIG. 4 shows a schematic diagram of an exposure state determining process according to an embodiment of this application. As shown in FIG. 4, an image with an overexposed pixel ratio $r_1>0.05$ may be predefined to be in an overexposed state in the computer device, and 0.05 herein is the first ratio threshold.

In addition, in this application, whether the current frame of image (that is, the first image) is in the underexposed state is determined according to whether there is a case in which a brightness value of most pixels is less than a medium brightness. For example, pixels with a grayscale value $Th_2$ or a grayscale value less than $Th_2$ are defined as underexposed pixels, and a ratio $r_2$ of pixels with a brightness value less than the medium brightness in a total image is calculated. A calculation formula is as follows:

$$r_2 = \frac{N[g < Th_2]}{N_{total}}$$

For example, in FIG. 4, an image with an underexposed pixel ratio $r_2>0.85$ is defined to be in an underexposed state, and 0.85 herein is the second ratio threshold. If the current frame of image satisfies neither the condition of the overexposed state, nor the condition of the underexposed state, the exposure state of the image is considered normal.

As shown in FIG. 4, the exposure state determining process is as follows:

S41. Obtain a current frame.

S42. Convert a current frame of image into a grayscale image.

S43. Determine whether an overexposed pixel ratio $r_1>0.05$ is true, if yes, perform S44; and if no, perform S45.

S44. Determine that the current frame is in an overexposed state.

S45. Determine whether an underexposed pixel ratio $r_2>0.85$ is true, if yes, perform S46; and if no, perform S47.

S46. Determine that the current frame is in an underexposed state.

S47. Determine that the current frame is in a normally-exposed state.

Step 305. Update the brightness reference value according to the exposure state of the first image, to obtain an updated brightness reference value.

In one embodiment, in response to that the exposure state of the first image is overexposure, the updating the brightness reference value according to the exposure state of the first image, to obtain an updated brightness reference value includes:

obtaining an adjustment value of the brightness reference value according to the overexposure ratio and a low brightness value threshold, the low brightness value threshold being an adjustment lower limit of the brightness reference value; and updating the brightness reference value according to the adjustment value, to obtain the updated brightness reference value.

If the brightness reference value is decreased without a lower limit, the brightness reference value is easily decreased to an extremely low value, resulting in underexposure during acquiring a next frame of image. Therefore, in one embodiment, a low brightness value threshold may be preset in the computer device, and the low brightness value threshold is used as a constraint for decreasing the brightness reference value.

The low brightness value threshold may be a brightness value preset by a developer.

In one embodiment, the obtaining an adjustment value of the brightness reference value according to the overexposure ratio and a low brightness value threshold includes:

calculating a first brightness adjustment coefficient according to the overexposure ratio; and calculating the adjustment value of the brightness reference value according to the first brightness adjustment coefficient and a first brightness value difference, the first brightness value difference being a difference between the brightness reference value and the low brightness value threshold.

In some embodiments, when the exposure state of the first image is underexposure, the updating the brightness reference value according to the exposure state of the first image, to obtain an updated brightness reference value includes:

obtaining an adjustment value of the brightness reference value according to a high brightness value threshold, the high brightness value threshold being an adjustment upper limit of the brightness reference value; and updating the brightness reference value according to the adjustment value, to obtain the updated brightness reference value.

If the brightness reference value is increased without an upper limit, the brightness reference value is easily increased to an extremely high value, resulting in overexposure during acquiring a next frame of image. Therefore, in one embodiment, a high brightness value threshold may be preset in the computer device, and the high brightness value threshold is used as a constraint for increasing the brightness reference value.

The high brightness value threshold may be a brightness value preset by a developer.

In some embodiments, the obtaining an adjustment value of the brightness reference value according to a high brightness value threshold includes:

calculating the adjustment value of the brightness reference value according to a specified second brightness adjustment coefficient and a second brightness value difference, the second brightness value difference being a difference between the high brightness value threshold and the brightness reference value.

One embodiment provides a solution in which a brightness reference value of a next frame is adjusted based on the current brightness reference value according to the exposure state of the current frame of image. The basic idea of the solution is to decrease the current brightness reference value for next automatic exposure when the current frame is in the overexposed state; increase the current brightness reference value for next exposure when the current frame is in the underexposed state; and maintain the brightness reference value unchanged when the current frame is in the normal status.

In some embodiments, during each adjustment, an adjustment range is calculated based on a current brightness reference value $t_{cur}$ by using a semi-empirical formula. First, a developer or maintenance personnel (such as a user of the microscope) sets an upper limit $t_H$ and a lower limit $t_L$ of the brightness reference value according to a specific task. When the current frame is in the overexposed state, an adjustment range $\Delta t$ of the brightness reference value is related to an overexposed pixel ratio $r_1$. A calculation formula is as follows:

$$\Delta t = -(1+\log_{20} r_1) \cdot (t_{cur} - t_L);$$

In this case, when the overexposed pixel ratio $r_1$ is slightly greater than an overexposed state determining threshold 0.05, $-(1+\log_{20} r_1)$ is a negative value close to 0, and the formula is equivalent to causing the brightness reference value to move to the lower limit $t_L$ of the brightness reference value by a small step. When the overexposed pixel ratio $r_1$ is close to 1, such case usually appears in an instant highlight scenario such as objective lens switching, and in this case, the value of $-(1+\log_{20} r_1)$ is close to $-1$, which means that the brightness reference value is directly set as the lower limit $t_L$ of the reference value. Experiments show that, the semi-empirical formula has relatively good adaptability in various cases.

In some embodiments, when the current frame is in the underexposed state, a calculation formula of the adjustment range $\Delta t$ of the brightness reference value is as follows:

$$\Delta t = 0.25 \cdot (t_H - t_{cur});$$

When the current frame is in the normal status, the adjustment range of the brightness reference value is $\Delta t=0$.

A brightness reference value $t_{next}$ of a next frame is calculated by using the following formula:

$$t_{next} = t_{cur} + \Delta t.$$

In the foregoing solution of this application, the semi-empirical formula summarized considering the usage is used to calculate the updated brightness reference value. In some embodiments, the computer device may calculate the updated brightness reference value in other manners. For example, the updated brightness reference value is determined according to an equalized average brightness value of a histogram.

Step 306. Control the exposure time of the image acquisition component according to the updated brightness reference value, to acquire a second image.

Figure 5:
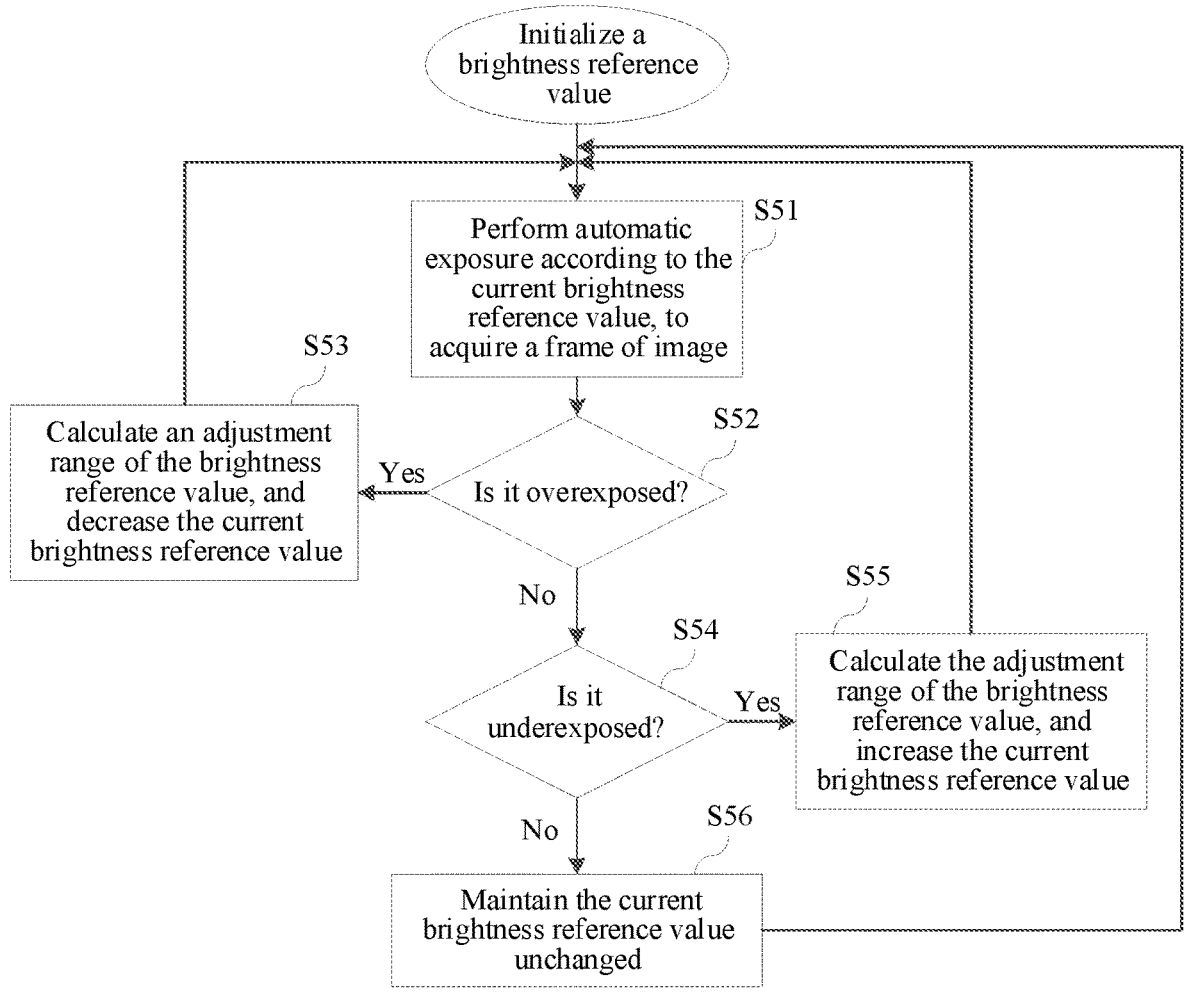
FIG. 5 is a flowchart of image acquisition according to the embodiment in FIG. 3.

For example, for the foregoing process of determining the exposure state of the first image, reference may be made to FIG. 5. FIG. 5 shows a flowchart of image acquisition according to an embodiment of this application. As shown in FIG. 5, a computer device initializes a brightness reference value of automatic exposure. First, the computer device performs automatic exposure according to the current brightness reference value, to acquire a frame of image (S51), then determines whether the image is overexposed (S52), and if the image is overexposed, calculates an adjustment range of the brightness reference value, decreases the current brightness reference value (S53), and acquires a subsequent image according to the decreased brightness reference value. If the image is not overexposed, the computer device further determines whether the current frame is underexposed (S54), if the current image is underexposed, calculates the adjustment range of the brightness reference value, increases the current brightness reference value (S55), and acquires a subsequent image according to the increased brightness reference value. If the current frame is not underexposed, it indicates that the current frame is normally exposed, and the computer device maintains the current brightness reference value unchanged (S56), and continues to acquire a subsequent image according to the brightness reference value.

In some embodiments, the computer device outputs the first image to an image processing device in response to that the exposure state of the first image is normal exposure, so that the image processing device performs a predetermined processing operation on the first image, the predetermined processing operation including at least one of the following operations:
performing pathological analysis on the first image;
displaying the first image; and
storing the first image.

In one embodiment, when the exposure state of the first image is normal exposure, it indicates that the first image satisfies a requirement for subsequent processing. In this case, the computer device may output the first image to the image processing device, so that the image processing device performs operations of pathological analysis, displaying, and storing, thereby improving an operation effect of the predetermined processing operation, for example, improving accuracy of the pathological analysis, and improving an image display effect.

In some embodiments, the computer device may discard the first image in response to that the exposure state of the first image is overexposure or underexposure.

In one embodiment, when the exposure state of the first image is not normal exposure, it indicates that the first image may not satisfy the requirement for subsequent processing. In this case, the computer device may discard the first image, and when an image with an exposure state of normal exposure is subsequently acquired, output the image with normal exposure to the image processing device.

In conclusion, according to the solution shown in one embodiment, the computer device may update a brightness reference value used during acquiring a previous frame of image according to an exposure state of the previous frame of acquired image, and acquire a next frame of image according to an updated brightness reference value, so that the brightness reference value is dynamically updated, and an exposure control effect during image acquisition in a complex environment is improved, thereby avoiding a loss of important image detail information of the next frame of image as much as possible.

According to the solution shown in one embodiment, an automatic exposure control method for a camera of a pathological microscope is provided. First, the exposure state of the current frame of image is determined according to brightness distribution thereof, and then the brightness reference value of the automatic exposure of the camera of the microscope is adjusted to an adaptive value quickly and adaptively, so that the loss of important image detail information of the next frame of image due to overexposure or underexposure can be avoided as much as possible, to prevent the introduction of unnecessary uncertainty into remote diagnosis and AI-assisted diagnosis made by the pathologist in a subsequent workflow.

Second, in the solution shown in one embodiment, quick evaluation of exposure state of the acquired image is implemented by performing simple statistical calculation according to image brightness (grayscale) distribution, so that a processing speed requirement for real-time tasks such as AI-assisted diagnosis and remote consultation can be satisfied.

In addition, the solution shown in one embodiment provides an implementation in which an adjustment range of a brightness reference value of a next frame is determined according to the brightness reference value and the overexposed (saturated) pixel ratio of the current frame. Compared with a method of estimating new reference values merely according to the brightness of the current frame, the brightness reference value of the current frame is additionally considered in this application. Compared with a method of fixing the adjustment range, the adjustment in this application is more flexible and efficient, and is more adaptable to both slow brightness changes in the field of view of the microscope during moving slides, and sharp brightness changes (from bright to black and then bright) in the field of view during switching objective lenses. In the solution shown in this application, the exposure state of the current frame of image can be determined according to brightness distribution thereof, and the brightness reference value of the automatic exposure of the camera can be adjusted to an adaptive value, to ensure that an adjustment speed does not affect an acquisition frame rate of the camera, and images with normal exposure can be acquired.

Figure 6:
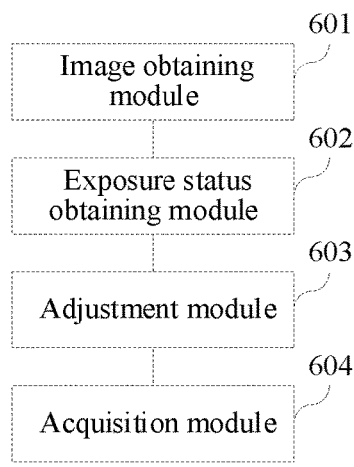
FIG. 6 is a structural block diagram of an image acquisition apparatus according to an exemplary embodiment of this application.

FIG. 6 is a structural block diagram of an image acquisition apparatus according to an exemplary embodiment of this application. The image acquisition apparatus may be applied to a computer device. For example, the computer device may be the microscope 120 or the image acquisition control device 180 in the foregoing system shown in FIG. 1. The image acquisition apparatus may include:

an image obtaining module 601, configured to obtain a latest acquired first image, the first image being an image acquired by controlling an exposure time of an image acquisition component according to a brightness reference value;

an exposure state obtaining module 602, configured to obtain an exposure state of the first image;

an adjustment module 603, configured to update the brightness reference value according to the exposure state of the first image, to obtain an updated brightness reference value; and an acquisition module 604, configured to control the exposure time of the image acquisition component according to the updated brightness reference value, to acquire a second image.

In one embodiment, the exposure state obtaining module 602 includes:

a grayscale processing unit, configured to perform grayscale processing on the first image, to obtain a grayscale image of the first image;

a ratio obtaining unit, configured to obtain a ratio of pixels that satisfy a specified condition in the grayscale image of the first image; and a status obtaining unit, configured to obtain the exposure state of the first image according to the ratio of the pixels that satisfy the specified condition.

In one embodiment, the specified condition includes an overexposure condition and an underexposure condition, the overexposure condition is that a grayscale value is greater than a first grayscale threshold, and the underexposure condition is that a grayscale value is less than a second grayscale threshold; and the status obtaining unit is configured to:

obtain that the exposure state of the first image is overexposure in response to that an overexposure ratio is higher than a first ratio threshold, the overexposure ratio being a ratio of pixels that satisfy the overexposure condition in the grayscale image of the first image;

obtain that the exposure state of the first image is underexposure in response to that an underexposure ratio is higher than a second ratio threshold, the underexposure ratio being a ratio of pixels that satisfy the underexposure condition in the grayscale image of the first image; and obtain that the exposure state of the first image is normal exposure in response to that the overexposure ratio is not higher than the first ratio threshold, and the underexposure ratio is not higher than the second ratio threshold.

In one embodiment, the adjustment module 603 is configured to:

obtain an adjustment value of the brightness reference value according to the overexposure ratio and a low brightness value threshold in response to that the exposure state of the first image is overexposure, the low brightness value threshold being an adjustment lower limit of the brightness reference value; and update the brightness reference value according to the adjustment value, to obtain the updated brightness reference value.

In one embodiment, during obtaining the adjustment value of the brightness reference value according to the overexposure ratio and the low brightness value threshold, the adjustment module 603 is configured to:

calculate a first brightness adjustment coefficient according to the overexposure ratio; and calculate the adjustment value of the brightness reference value according to the first brightness adjustment coefficient and a first brightness value difference, the first brightness value difference being a difference between the brightness reference value and the low brightness value threshold.

In one embodiment, the adjustment module 603 is configured to:

obtain an adjustment value of the brightness reference value according to a high brightness value threshold in response to that the exposure state of the first image is underexposure, the high brightness value threshold being an adjustment upper limit of the brightness reference value; and update the brightness reference value according to the adjustment value, to obtain the updated brightness reference value.

In one embodiment, during obtaining the adjustment value of the brightness reference value according to the high brightness value threshold, the adjustment module 603 is configured to calculate the adjustment value of the brightness reference value according to a specified second brightness adjustment coefficient and a second brightness value difference, the second brightness value difference being a difference between the high brightness value threshold and the brightness reference value.

In one embodiment, the apparatus further includes:

an image output module, configured to output the first image to an image processing device in response to that the exposure state of the first image is normal exposure, so that the image processing device performs a predetermined processing operation on the first image, the predetermined processing operation including at least one of the following operations:

performing pathological analysis on the first image;

displaying the first image; and storing the first image.

In one embodiment, the apparatus further includes:

a discarding module, configured to discard the first image in response to that the exposure state of the first image is overexposure or underexposure.

In conclusion, according to the solutions shown in one embodiment, the computer device may update a brightness reference value used during acquiring a previous frame of image according to an exposure state of the previous frame acquired image, and acquire a next frame of image according to an updated brightness reference value, so that the brightness reference value is dynamically updated, and an exposure control effect during image acquisition in a complex environment is improved, thereby avoiding a loss of important image detail information of the next frame of image as much as possible.

Figure 7:
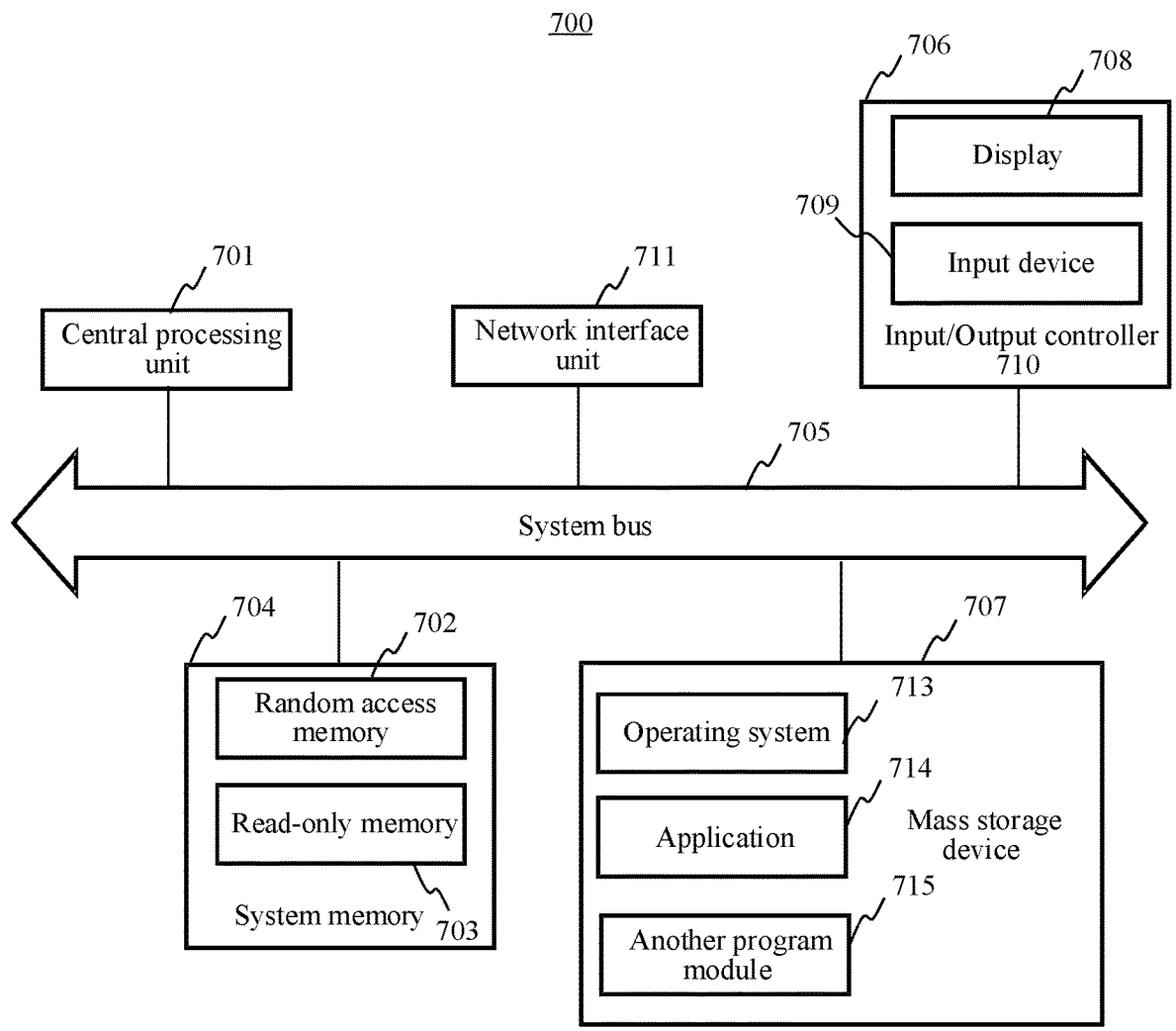
FIG. 7 is a schematic structural diagram of a computer device according to an exemplary embodiment.

FIG. 7 is a schematic structural diagram of a computer device according to an exemplary embodiment. The computer device may be implemented as a terminal or a server. For example, the terminal may be a terminal 140 in the system shown in FIG. 1, and the server may be the server 160 in the system shown in FIG. 1.

The computer device 700 includes a central processing unit (CPU) 701, a system memory 704 including a random access memory (RAM) 702 and a read-only memory (ROM) 703, and a system bus 705 connecting the system memory 704 and the CPU 701. The computer device 700 further includes a basic input/output (I/O) system 706 configured to transmit information between components in a computer, and a mass storage device 707 configured to store an operating system 713, an application 714, and another program module 715.

The basic I/O system 706 includes a display 708 configured to display information and an input device 709 such as a mouse or a keyboard that is configured for information inputting by a user. The display 708 and the input device 709 are both connected to the CPU 701 by using an input/output controller 710 connected to the system bus 705. The basic I/O system 706 may further include the input/output controller 710, to receive and process inputs from a plurality of other devices, such as a keyboard, a mouse, and an electronic stylus. Similarly, the input/output controller 77 further provides an output to a display screen, a printer, or another type of output device.

The mass storage device 707 is connected to the CPU 701 by using a mass storage controller (not shown) connected to the system bus 705. The mass storage device 707 and an associated computer-readable medium provide non-volatile storage for the computer device 700. In other words, the mass storage device 707 may include a computer-readable medium (not shown) such as a hard disk or a CD-ROM drive.

Without loss of generality, the computer-readable medium may include a computer storage medium and a communications medium. The computer storage medium includes volatile and non-volatile media, and removable and non-removable media implemented by using any method or technology used for storing information such as computer-readable instructions, data structures, program modules, or other data. The computer-storage medium includes a RAM, a ROM, an erasable programmable ROM (EPROM), an electrically erasable programmable ROM (EEPROM), a flash memory or another solid-state storage technology, a CD-ROM, a DVD or another optical storage, a magnetic cassette, a magnetic tape, or a magnetic disk storage or another magnetic storage device. Certainly, a person skilled in the art may learn that the computer storage medium is not limited to the foregoing several types. The system memory 704 and the mass storage device 707 may be collectively referred to as a memory.

The computer device 700 may be connected to the Internet or another network device by using a network interface unit 711 connected to the system bus 705.

The memory further includes one or more programs. The one or more programs are stored in the memory. The CPU 701 executes the one or more programs to perform all or some steps of the method shown in FIG. 2 or FIG. 3.

An embodiment of this application further provides a computer device including a memory and a processor, the memory storing at least one instruction, at least one program, a code set, or an instruction set, the at least one instruction, the at least one program, the code set, or the instruction set being loaded and executed by the processor, to perform all or some steps of the method shown in FIG. 2 or FIG. 3

An embodiment of this application further provides a computer-readable storage medium, storing at least one instruction, at least one program, a code set, or an instruction set, the at least one instruction, the at least one program, the code set, or the instruction set being loaded and executed by a processor to perform all or some steps of the method shown in FIG. 2 or FIG. 3.

An embodiment of this application further provides a computer program product or a computer program, including computer instructions, the computer instructions being stored in a computer-readable storage medium. A processor of a computer device reads the computer instructions from the computer-readable storage medium, and the processor executes the computer instructions, to cause the computer device to perform all or some steps of the method shown in FIG. 2 or FIG. 3.

A person of ordinary skill in the art may understand that all or some steps of the methods in the foregoing embodiments may be implemented by a computer program product or a computer program to instruct relevant hardware. The computer program product or the computer program may be stored in a computer-readable storage medium. The computer-readable storage medium may be the computer-readable storage medium included in the memory in the foregoing embodiments, or may be a computer-readable storage medium that exists independently and that is not assembled in a terminal.

The term module, and other similar terms such as subunit, unit, submodule, etc., in this disclosure may refer to a software unit, a hardware unit, or a combination thereof. A software module (e.g., computer program) may be developed using a computer programming language. A hardware module may be implemented using processing circuitry and/or memory. Each module can be implemented using one or more processors (or processors and memory). Likewise, a processor (or processors and memory) can be used to implement one or more modules. Moreover, each unit can be part of an overall module that includes the functionalities of the module.

In some embodiments, the computer-readable storage medium may include: a read-only memory (ROM), a random access memory (RAM), a solid state drive (SSD), an optical disc, or the like. The RAM may include a resistance random access memory (ReRAM) and a dynamic random access memory (DRAM). The sequence numbers of the foregoing embodiments of this application are merely for description purpose but do not imply the preference among the embodiments.

The foregoing descriptions are merely exemplary embodiments of this application, and are not intended to limit this application. Any modification, equivalent replacement, improvement and the like made within the spirit and principle of this application shall fall within the protection scope of this application.

What is claimed is:

1. An image acquisition method, performed by a computer device, the method comprising:
    obtaining a first image and a grayscale image of the first image, the first image being an image acquired by controlling an exposure time of an image acquisition component according to a brightness reference value;
    obtaining an exposure state of the first image;
    determining that the exposure state of the first image is overexposure in response to that an overexposure ratio is higher than a first ratio threshold, the overexposure ratio being a ratio of pixels that satisfy an overexposure condition in the grayscale image of the first image;

updating the brightness reference value according to the exposure state of the first image, to obtain an updated brightness reference value, comprising:
    calculating a first brightness adjustment coefficient according to the overexposure ratio and calculating an adjustment value of the brightness reference value according to the first brightness adjustment coefficient and a first brightness value difference, the first brightness value difference being a difference between the brightness reference value and a low brightness value threshold; and
    updating the brightness reference value according to the adjustment value, to obtain the updated brightness reference value;
controlling the exposure time of the image acquisition component according to the updated brightness reference value; and
acquiring a second image.

2. The method according to claim 1, wherein the obtaining an exposure state of the first image comprises:
    performing grayscale processing on the first image, to obtain the grayscale image of the first image;
    obtaining a ratio of pixels that satisfy a specified condition in the grayscale image of the first image; and
    obtaining the exposure state of the first image according to the ratio of the pixels that satisfy the specified condition.

3. The method according to claim 2, wherein the specified condition comprises an overexposure condition and an underexposure condition, the overexposure condition is that a grayscale value is greater than a first grayscale threshold, and the underexposure condition is that a grayscale value is less than a second grayscale threshold; and
    the obtaining the exposure state of the first image according to the ratio of the pixels that satisfy the specified condition comprises:
    determining that the exposure state of the first image is underexposure in response to that an underexposure ratio is higher than a second ratio threshold, the underexposure ratio being a ratio of pixels that satisfy the underexposure condition in the grayscale image of the first image; and
    determining that the exposure state of the first image is normal exposure in response to that the overexposure ratio is not higher than the first ratio threshold, and the underexposure ratio is not higher than the second ratio threshold.

4. The method according to claim 3, wherein when the exposure state of the first image is overexposure, the updating the brightness reference value according to the exposure state of the first image, to obtain an updated brightness reference value comprises:
    obtaining the adjustment value of the brightness reference value according to the overexposure ratio and the low brightness value threshold, the low brightness value threshold being an adjustment lower limit of the brightness reference value; and
    updating the brightness reference value according to the adjustment value, to obtain the updated brightness reference value.

5. The method according to claim 3, wherein when the exposure state of the first image is underexposure, the updating the brightness reference value according to the exposure state of the first image, to obtain an updated brightness reference value comprises:
    obtaining the adjustment value of the brightness reference value according to a high brightness value threshold, the high brightness value threshold being an adjustment upper limit of the brightness reference value; and
    updating the brightness reference value according to the adjustment value, to obtain the updated brightness reference value.

6. The method according to claim 5, wherein the obtaining the adjustment value of the brightness reference value according to a high brightness value threshold comprises:
    calculating the adjustment value of the brightness reference value according to a specified second brightness adjustment coefficient and a second brightness value difference, the second brightness value difference being a difference between the high brightness value threshold and the brightness reference value.

7. The method according to claim 3, further comprising:
    outputting the first image to an image processing device in response to the exposure state of the first image being normal exposure, the image processing device processing the first image by performing one of the following operations:
    performing pathological analysis on the first image;
    displaying the first image; and
    storing the first image.

8. The method according to claim 3, further comprising:
    discarding the first image in response to the exposure state of the first image being overexposure or underexposure.

9. An image acquisition apparatus, comprising a memory storing computer instructions and a processor configured to execute the computer instructions to:
    obtain a first image and a grayscale image of the first image, the first image being an image acquired by controlling an exposure time of an image acquisition component according to a brightness reference value;
    obtain an exposure state of the first image;
    determine that the exposure state of the first image is overexposure in response to that an overexposure ratio is higher than a first ratio threshold, the overexposure ratio being a ratio of pixels that satisfy an overexposure condition in the grayscale image of the first image;
    update the brightness reference value according to the exposure state of the first image, to obtain an updated brightness reference value, comprising:
        calculate a first brightness adjustment coefficient according to the overexposure ratio and calculate an adjustment value of the brightness reference value according to the first brightness adjustment coefficient and a first brightness value difference, the first brightness value difference being a difference between the brightness reference value and a low brightness value threshold; and
        update the brightness reference value according to the adjustment value, to obtain the updated brightness reference value; and
    control the exposure time of the image acquisition component according to the updated brightness reference value, to acquire a second image.

10. The apparatus according to claim 9, wherein the processor is further configured to:
    perform grayscale processing on the first image, to obtain the grayscale image of the first image;
    obtain a ratio of pixels that satisfy a specified condition in the grayscale image of the first image; and
    obtain the exposure state of the first image according to the ratio of the pixels that satisfy the specified condition.

11. The apparatus according to claim 10, wherein the specified condition comprises an overexposure condition and an underexposure condition, the overexposure condition is that a grayscale value greater than a first grayscale threshold, and the underexposure condition is that a grayscale value less than a second grayscale threshold; and the processor is further configured to:
determine that the exposure state of the first image is underexposure in response to that an underexposure ratio is higher than a second ratio threshold, the underexposure ratio being a ratio of pixels that satisfy the underexposure condition in the grayscale image of the first image; and
determine that the exposure state of the first image is normal exposure in response to that the overexposure ratio is not higher than the first ratio threshold, and the underexposure ratio is not higher than the second ratio threshold.

12. The apparatus according to claim 11, wherein the processor is further configured to:
obtain the adjustment value of the brightness reference value according to the overexposure ratio and the low brightness value threshold in response to that the exposure state of the first image is overexposure, the low brightness value threshold being an adjustment lower limit of the brightness reference value; and
update the brightness reference value according to the adjustment value, to obtain the updated brightness reference value.

13. The apparatus according to claim 11, wherein the processor is further configured to:
obtain the adjustment value of the brightness reference value according to a high brightness value threshold in response to that the exposure state of the first image is underexposure, the high brightness value threshold being an adjustment upper limit of the brightness reference value; and
update the brightness reference value according to the adjustment value, to obtain the updated brightness reference value.

14. The apparatus according to claim 13, wherein
the processor is further configured to calculate the adjustment value of the brightness reference value according to a specified second brightness adjustment coefficient and a second brightness value difference, the second brightness value difference being a difference between the high brightness value threshold and the brightness reference value.

15. The apparatus according to claim 11, wherein the processor is further configured to:
output the first image to an image processing device in response to that the exposure state of the first image is normal exposure, so that the image processing device performs a processing operation on the first image, the processing operation comprising at least one of:
performing pathological analysis on the first image;
displaying the first image; and
storing the first image.

16. The apparatus according to claim 11, wherein processor is further configured to:
discard the first image in response to that the exposure state of the first image is overexposure or underexposure.

17. A non-transitory computer-readable storage medium, storing at least one instruction, at least one program, a code set, or an instruction set, the at least one instruction, the at least one program, the code set, or the instruction set being loaded and executed by a processor to perform the image acquisition method comprising:
obtaining a first image and a grayscale image of the first image, the first image being an image acquired by controlling an exposure time of an image acquisition component according to a brightness reference value;
obtaining an exposure state of the first image;
determining that the exposure state of the first image is overexposure in response to that an overexposure ratio is higher than a first ratio threshold, the overexposure ratio being a ratio of pixels that satisfy an overexposure condition in the grayscale image of the first image;
updating the brightness reference value according to the exposure state of the first image, to obtain an updated brightness reference value, comprising:
calculating a first brightness adjustment coefficient according to the overexposure ratio and calculating an adjustment value of the brightness reference value according to the first brightness adjustment coefficient and a first brightness value difference, the first brightness value difference being a difference between the brightness reference value and a low brightness value threshold; and
updating the brightness reference value according to the adjustment value, to obtain the updated brightness reference value;
controlling the exposure time of the image acquisition component according to the updated brightness reference value; and
acquiring a second image.

18. The non-transitory computer-readable storage medium according to claim 17, wherein the obtaining an exposure state of the first image comprises:
performing grayscale processing on the first image, to obtain the grayscale image of the first image;
obtaining a ratio of pixels that satisfy a specified condition in the grayscale image of the first image; and
obtaining the exposure state of the first image according to the ratio of the pixels that satisfy the specified condition.

* * * * *